United States Patent [19]

Youssefyeh

[11] Patent Number: 4,714,615

[45] Date of Patent: Dec. 22, 1987

[54] SKIN TREATMENT COMPOSITIONS COMPRISING UNOXIDIZED NERVE TISSUE

[76] Inventor: Rina Youssefyeh, 67 Amhurst Way, Princeton Jnc., N.J. 08550

[21] Appl. No.: 850,569

[22] Filed: Apr. 11, 1986

Related U.S. Application Data

[63] Continuation-in-part of Ser. No. 599,010, Apr. 11, 1984, abandoned.

[51] Int. Cl.$^4$ .............................................. A61K 35/12
[52] U.S. Cl. ..................... 424/95; 424/464; 514/844; 514/887
[58] Field of Search .................. 424/95, 464; 514/844, 514/887

[56] References Cited

U.S. PATENT DOCUMENTS 2,717,227  9/1955  Dawson ................................ 424/95
4,094,973  6/1978  Robertson ......................... 424/95 X

OTHER PUBLICATIONS

Chem. Abst. 83:129194j (1975), Phospholipid Composition of Proteolipids From the White Matter of Various Parts of the Brain, Spinal Cord and Sciatic Nerve of Dogs, Manukyan, K. G.

Chem. Abst. 75:73500w (1971), Phospholipid Composition of White Matter of Different Parts of Dog Brain and Spinal Cord and the Sciatic Nerve. Manukyan, K. G., Kirakosyan, L. G.

Cosmetics: Science & Technology, 2nd Ed. vol. I, Wiley, NY, pp. 336-339, Balsam, et al.

Primary Examiner—Sidney Marantz
Assistant Examiner—Shawn P. Foley

[57] ABSTRACT

Method for retexturizing and smoothening the skin comprising topically applying to the skin a composition comprising from about 1.5 to about 2.5 parts by weight of a powdery, cosmetically acceptable inorganic material, such as calcium carbonate, and about 1 part by weight of nerve tissue such as the spinal cord.

5 Claims, No Drawings

SKIN TREATMENT COMPOSITIONS COMPRISING UNOXIDIZED NERVE TISSUE

This application is a continuation-in-part of copending application Ser. No. 599,010, filed Apr. 11, 1984 now abandoned. This invention relates to cosmetic compositions. It particularly relates to compositions for retexturizing and smoothening the skin.

BACKGROUND OF THE INVENTION

Although adequate washing with soap and water will remove surface grime, facial makeup and oils from the face, it is well recognized that for this purpose the use of specially formulated cleansing creams and lotions has certain advantages. For example, the special chemical nature of facial makeup leads to the use of specific formulations for dissolving or lifting the oily binding materials in the makeup which hold the pigments therein, as well as the grime settling thereon, from the skin.

Natural skin oil, sebum, is a product of normal metabolism and is excreted from sebaceous glands in the skin. These oils tend to solidify over the sebaceous orifice to form hardened plaques which are difficult to remove by washing with only soap and water. Even scrubbing with soap and water fails to remove these plaques. Furthermore, although the plaques are formed from fatty materials they are surprisingly resistant to dissolution in the usual solvents for fats such as acetone, chloroform, glycerine, kerosene, hexane, dioxane, trichloroethylene, ethanol, and the like, which readily remove surface oils on the skin but are inefficient in dissolving the solid plaques.

The formation of these plaques gives the skin a rough and aged appearance, and the appearance is further marred by the constant drying of the outermost epidermal cells. These dead dry cells remain on the skin adding to the rough appearance.

Preparations such as skin lotions, creams and the like are available for cleaning the skin and removing plaques. Some of these preparations contain abrasive materials such as borax particles which aid in the removal of plaques as well as the rough dead skin. However, although these compositions may be effective in removing the plaques and cell debris, they do not leave the skin with a smooth appearance and feel.

DESCRIPTION OF THE INVENTION

It is an object of this invention to provide a composition and a method by which undesirable material adhering to the skin may be removed.

It is another object of this invention to provide a composition and a method by which undesirable material adhering to the skin may be removed and the skin left with a smooth appearance and feel.

It is a further object of this invention to provide compositions for removing undesirable matter from the skin which can be conveniently applied to the skin.

Other objects will appear from the discussion which follows.

In accordance with this invention there are provided compositions comprised of a cosmetically acceptable inorganic material and nerve tissue. Cosmetically acceptable materials, such as the cosmetically acceptable inorganic materials used in the practice of this invention, are pharmaceutically inert with respect to the skin.

Cosmetically acceptable inorganic materials suitable for the practice of this invention include calcium salts such as the acetate, carbonate, formate, gluconate, lactate, oxalate, phosphate, and stannate, calcium carbonate, magnesium carbonate, zinc carbonate, magnesium aluminum silicate, silica, zinc aluminum silicate, talc and the like. These materials, or mixtures thereof, are used in finely powdered form. Calcium carbonate (USP grade) is preferred.

The nerve tissue may be obtained from nerves per se, spinal cords, and brains. Spinal cords are preferred.

In preparing the compositions of this invention from about 1.5 to about 2.5 parts by weight of the powdery cosmetically acceptable inorganic material was mixed with about 1 part by weight of unoxidized nerve tissue by grinding at a temperature from about 20° to about 70° C. until a doughy mix was obtained. The doughy mix may be formed into tablets having a disc-like shape and a thickness from about ⅛ to about ⅜" and a diameter from about ½ to about 1", or dried at a temperature from about 20° to about 70° C. for about 3 to 24 hours. A solid, whitish material was obtained on drying. This material may, when desired, be ground to a powder which can be used directly or put into tablets, creams or lotions.

The invention will become clearer from the examples which follow. These examples are given only by way of illustration and are not to be considered as limiting.

EXAMPLE 1

To 30 g calcium carbonate powder (USP) was added 15 g of cattle spinal cord from which the lamina had been removed and which had been washed well with water to remove any adhering tissue and blood stains. This mixture of calcium carbonate and the spinal cord was ground at about 70° C. until a substantially uniform doughy mixture was obtained. The ground mixture was air dried at ambient temperatures (about 20° to 25° C.) for about 24 hours to form a solid white material.

EXAMPLE 2

The procedure of example 1 was repeated, except that the drying operation was carried out by heating in a vacuum oven at about 45° C. for about 8 hours.

EXAMPLE 3

The procedure of example 1 was repeated, except that the grinding operation was carried out at about 50° C.

EXAMPLE 4

The procedure of example 1 was repeated through the grinding stage. The doughy mixture was then shaped into tablets of disc-like shape having a thickness of about ¼" and a diameter of about ¾". The tablets were then dried by heating at about 70° C. for about 3 hours.

EXAMPLE 5

The procedure of example 4 was repeated, except that the tablets had a thickness of about ⅛" and a diameter of about ¾".

EXAMPLE 6

The solid white material of example 1 was ground to a powder and incorporated in a lotion of the following composition using standard techniques for the preparation of lotions:

| Material | Parts by Weight |
| --- | --- |
| Triethanolaminelauryl sulfate | 5 |
| Mineral oil 65/75 | 20 |
| Beeswax | 2 |
| Calcium carbonate-spinal cord mixture | 20 |
| Preservative | 0.1 |
| Water q.s. | 100 |

A suitable preservative for use in this composition and in the composition of example 7 below is ethyl hydroxy-benzoate.

EXAMPLE 7

A cream of the following composition containing the powdered product of example 1 was prepared using standard techniques. The composition was as follows:

| Material | Parts by Weight |
| --- | --- |
| Beeswax | 10 |
| Mineral oil | 40 |
| Paraffin | 10 |
| Ozokerite | 5 |
| Calcium carbonate-spinal cord mixture | 10 |
| Preservative | 0.1 |
| Water q.s. | 100 |

The tablets, powder, lotion and cream remained stable, showing no signs of disintegration or spoilage, after standing at ambient temperature (about 20° to 25° C.) for 6 months.

When using the compositions of this invention, the skin is first rinsed with warm water and the cmposition in the form of a powder, tablet, cream or lotion is rubbed into the wet skin and the skin is then gently massaged. The material is then rinsed off with warm water and the skin dried. The product may be applied from one to seven times weekly. It has been found that after the treatment with the composition of the present invention the skin has a clean smooth appearance and feel.

What is claimed is:

1. A method for cleansing human skin comprising topically applying to said human skin a composition comprising: from 1.5 to 2.5 parts by weight of a powdery, cosmetically acceptable inorganic substance selected from the group consisting of calcium acetate, calcium carbonate, calcium formate, calcium gluconate, calcium lactate, calcium oxalate, calcium phosphate, calcium stannate, magnesium carbonate, magnesium aluminum silicate, zinc carbonate, zinc aluminum silicate, silica, talc and mixtures thereof and 1 part by weight of unoxidized cattle spinal cord.

2. The method of claim 1 wherein said cosmetically acceptable substance is calcium carbonate.

3. The method of claim 1 wherein said composition comprises 2 parts by weight of calcium carbonate and 1 part by weight of spinal cord.

4. The method of claim 1 wherein said composition is in the form of a disc-shaped tablet having a thickness from about ⅛" to about ⅜" and a diameter from about ½" to about 1".

5. A method for cleansing human skin comprising topically applying to said human skin a composition comprising: from 1.5 to 2.5 parts by weight of a powdery, cosmetically acceptable inorganic substance selected from the group consisting of calcium acetate, calcium carbonate, calcium formate, calcium gluconate, calcium lactate, calcium oxalate, calcium phosphate, calcium stannate, magnesium carbonate, magnesium aluminum silicate, zinc carbonate, zinc aluminum silicate, silica, talc and mixtures thereof and 1 part by weight of unoxidized cattle brain.

* * * * *